United States Patent
Urban et al.

(10) Patent No.: US 12,169,928 B2
(45) Date of Patent: Dec. 17, 2024

(54) ULTRASOUND IMAGING OF VASCULATURE

(71) Applicants: IMEC VZW, Leuven (BE); Katholieke Universiteit Leuven, KU Leuven R&D, Leuven (BE); VIB VZW, Zwijnaarde (BE)

(72) Inventors: Alan Urban, Brussels (BE); Gabriel Montaldo, Brussels (BE)

(73) Assignees: IMEC VZW, Leuven (BE); Katholieke Universiteit Leuven, Leuven (BE); KU Leuven R&D, Zwijnaarde (BE)

( * ) Notice: Subject to any disclaimer, the term of this patent is extended or adjusted under 35 U.S.C. 154(b) by 511 days.

(21) Appl. No.: 17/430,039

(22) PCT Filed: Feb. 14, 2020

(86) PCT No.: PCT/EP2020/053898
§ 371 (c)(1),
(2) Date: Aug. 11, 2021

(87) PCT Pub. No.: WO2020/165412
PCT Pub. Date: Aug. 20, 2020

(65) Prior Publication Data
US 2022/0138938 A1 May 5, 2022

(30) Foreign Application Priority Data
Feb. 15, 2019 (EP) .................... 19157501

(51) Int. Cl.
*G06T 7/00* (2017.01)
*A61B 8/08* (2006.01)
*G06T 5/73* (2024.01)

(52) U.S. Cl.
CPC .......... *G06T 7/0012* (2013.01); *A61B 8/0891* (2013.01); *A61B 8/488* (2013.01);
(Continued)

(58) Field of Classification Search
CPC ................. G06T 7/0012; G06T 5/003; G06T 2207/10132; G06T 2207/30101;
(Continued)

(56) References Cited

U.S. PATENT DOCUMENTS 10,533,977 B2 * 1/2020 Paul ................ G01N 29/11
2018/0220997 A1 8/2018 Song et al.
(Continued)

OTHER PUBLICATIONS

Spatiotemporal Clutter Filtering of Ultrafast Ultrasound Data Highly Increases Doppler and fUltrasound Sensitivity (Year: 2015).*
(Continued)

*Primary Examiner* — Michael Robert Cammarata
*Assistant Examiner* — Pardis Sohraby
(74) *Attorney, Agent, or Firm* — McDonnell Boehnen Hulbert & Berghoff LLP

(57) ABSTRACT

The current invention concerns a method, a computer system, and a computer program product for blood vessel image extraction from ultrasound signals, and a method and apparatus for ultrasound imaging A set of ultrasound signals at successive times in a plurality of spatial points is obtained. The ultrasound signals are decomposed as a sum of terms. Each term consists of a time-independent spatial component image factor and a space-independent temporal component signal. The spatial component images are mutually orthonormal. The temporal component signals are mutually orthogonal. A sharpened spatial image for each of multiple spatial component images is determined. A processed image being a bilinear combination of multiple sharpened spatial images is generated.

20 Claims, 5 Drawing Sheets

(52) U.S. Cl.
CPC .............. *A61B 8/5207* (2013.01); *G06T 5/73* (2024.01); *G06T 2207/10132* (2013.01); *G06T 2207/30101* (2013.01)

(58) Field of Classification Search
CPC ..... G06T 7/0014; A61B 8/0891; A61B 8/488; A61B 8/5207; A61B 8/5269; A61B 8/5253; G01S 7/52047; G01S 7/52077; G01S 15/8977
USPC ........................................................ 382/131
See application file for complete search history.

(56) References Cited

U.S. PATENT DOCUMENTS

| | | | | |
|---|---|---|---|---|
| 2018/0322632 | A1* | 11/2018 | Barnes | G16H 30/40 |
| 2018/0325493 | A1* | 11/2018 | Takeda | G01S 15/8977 |
| 2019/0129026 | A1* | 5/2019 | Sumi | G01S 7/52038 |
| 2020/0184614 | A1* | 6/2020 | Zhang | G01S 15/8981 |
| 2020/0315584 | A1* | 10/2020 | Wissel | A61B 8/08 |
| 2021/0390698 | A1* | 12/2021 | Auvray | A61B 8/4416 |
| 2022/0096056 | A1* | 3/2022 | Alizad | A61B 8/5276 |

OTHER PUBLICATIONS

Macé, Emilie, Gabriel Montaldo, Ivan Cohen, Michel Baulac, Mathias Fink, and Mickael Tanter. "Functional ultrasound imaging of the brain." Nature methods 8, No. 8 (2011): 662-664.

Demené, Charlie, Thomas Deffieux, Mathieu Pernot, Bruno-Félix Osmanski, Valérie Biran, Jean-Luc Gennisson, Lim-Anna Sieu et al. "Spatiotemporal clutter filtering of ultrafast ultrasound data highly increases Doppler and fUltrasound sensitivity." IEEE transactions on medical imaging 34, No. 11 (2015): 2271-2285.

PCT International Search Report and Written Opinion, Application No. PCT/EP2020/053898, mailed Mar. 26, 2020, 12 pages.

Song, Pengfei, Armando Manduca, Joshua D. Trzasko, and Shigao Chen. "Ultrasound small vessel imaging with block-wise adaptive local clutter filtering." IEEE transactions on medical imaging 36, No. 1 (2016): 251-262.

Bayat, Mahdi, Azra Alizad, and Mostafa Fatemi. "Multi-rate higher order singular value decomposition for enhanced non-contrast ultrasound Doppler imaging of slow flow." In 2018 IEEE 15th International Symposium on Biomedical Imaging (ISBI 2018), pp. 1178-1181. IEEE, 2018.

* cited by examiner

ULTRASOUND IMAGING OF VASCULATURE

CROSS-REFERENCE TO RELATED APPLICATIONS

This application is a U.S. national phase application of international application no. PCT/EP2020/053898 filed on Feb. 14, 2020, which claims priority to European patent application no. EP 19157501.8 filed on Feb. 15, 2019, the contents of both being incorporated by reference in their entirety.

FIELD OF THE DISCLOSURE

The invention pertains to ultrasound Doppler imaging of vasculature.

BACKGROUND

Ultrasound Doppler imaging is an important imaging technique for blood vasculature. Traditionally, ultrasound imaging is realized via focused beams, wherein multiple lines are scanned sequentially in time. Measurements for different lines are thereby not coherent in time. Moreover, scanning a two- or three-dimensional area requires a considerable amount of time.

E. Mace et al., Nature Methods 8(8), 662-664 (2011), doi: 10.1038/nmeth.1641 and E. Mace et al., IEEE Transactions on Ultrasonics, Ferroelectrics, and Frequency Control 60(3), 492-506 (2013), doi: 10.1109/tuffc.2013.2592 disclose ultrasound power Doppler imaging via plane waves, which allows ultrafast and time-coherent imaging of a two- or three-dimensional area. Backscattered echoes of a set of plane wave emissions tilted at different angles are coherently compounded to improve quality. Each compound image provides a time sample (denoted $t_j$) of the complex IQ signal, alternatively called spatiotemporal cineloop, $s(r_i,t_j)$ for each pixel $r_i$. Via a high-pass filter, temporal discrimination of slower tissue movement and faster red blood cell movement is performed per pixel. The technique is used for functional ultrasound imaging of brain vasculature.

C. Demene et al., IEEE Transactions on Medical Imaging 34(11), 2271-2285 (2015), doi: 10.1109/tmi.2015.2428634 and A. Urban et al., Jacobs Journal of Molecular and Translational Medicine 1(1), 007 (2015) disclose an improved discrimination of tissue and red blood cell movement. When (relative) tissue motion is important (e.g. free hand imaging, vibrations or cardiac movement) or when blood flow velocities become slow (e.g. in small vessels), tissue and red blood cell movement are not separable based on a frequency cut-off. Instead, a spatiotemporal singular value decomposition of the complex IQ signal $s(ri,tj) = \sum_{k=1}^{N} \lambda_k p_k(r_i) a_k(t_j)$ allows to isolate tissue movement from blood flow movement. Tissue movement is spatially coherent and more energetic, resulting in the largest singular value contributions of the decomposition, which may be eliminated to obtain the blood signal.

The scattering of waves from a small vessel may result in an image with a broadened representation of the small vessel. In case from a certain point of view small vessels cross or are proximate, it may no longer be possible to discern the separate vessels.

The present invention aims to provide an improved representation of small vessels in an ultrasound Doppler image.

The present invention aims to resolve at least some of the problems mentioned above.

SUMMARY OF THE INVENTION

In a first aspect, the present invention provides a method for blood vessel image extraction from ultrasound signals.

In a second aspect, the present invention provides a method for ultrasound imaging.

In a third aspect, the present invention provides a computer system for blood vessel image extraction from ultrasound signals.

In a fourth aspect, the present invention provides a computer program product for blood vessel image extraction from ultrasound signals.

In a fifth aspect, the present invention provides an apparatus for ultrasound imaging of vasculature.

The present invention enables resolving small vessels in ultrasound imaging. The present invention in particular solves undesirable blurring when ultrasound waves are scattered off small vessels.

DETAILED DESCRIPTION OF THE INVENTION

Figure 1:
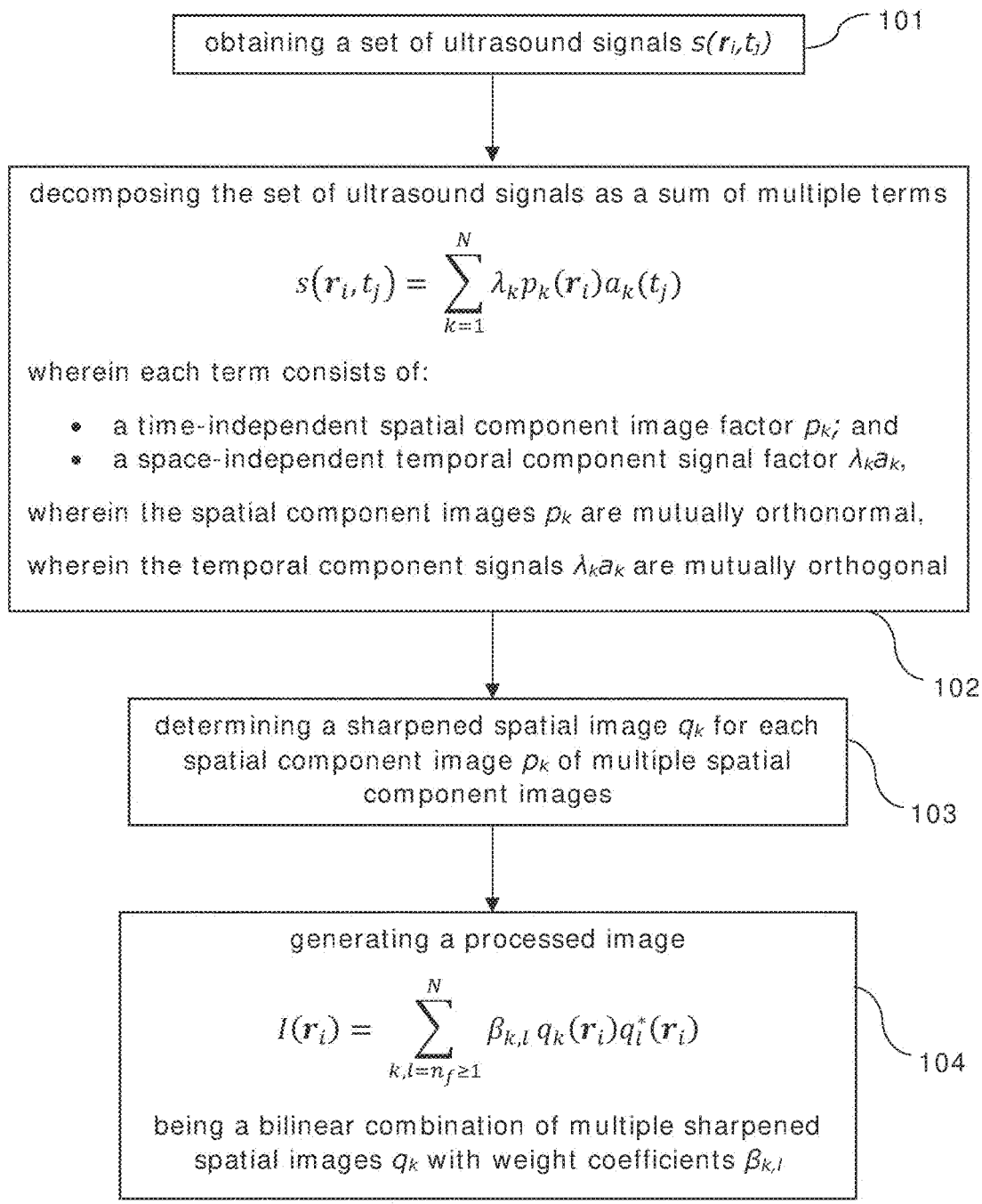
FIG. 1 is a block diagram of a method, according to an example.

The present invention concerns a method, a computer system, and a computer program product for blood vessel image extraction from ultrasound signals. The present invention furthermore concerns a method and an apparatus for ultrasound imaging. The invention has been summarized in the corresponding section above. In what follows, the invention is described in detail, preferred embodiments are discussed, and the present invention is illustrated by means of examples.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

"A", "an", and "the" as used herein refers to both singular and plural referents unless the context clearly dictates otherwise. By way of example, "a compartment" refers to one or more than one compartment.

"Comprise", "comprising", and "comprises" as used herein are synonymous with "include", "including", "includes" or "contain", "containing", "contains" and are inclusive or open-ended terms that specify the presence of what follows (e.g. component) and do not exclude or preclude the presence of additional, non-recited components, features, elements, members, steps, known in the art or disclosed therein.

"Based on" as used herein is synonymous with "based at least in part on" and is an inclusive or open-ended term that specifies the presence of what follows and does not exclude of preclude the presence of additional, non-recited components, features, elements, members, steps, known in the art or disclosed therein.

In a first aspect, the present invention provides a method for blood vessel image extraction from ultrasound signals. The method comprises several steps. A set of ultrasound signals of biological tissue of a living subject comprising blood vessels is obtained. The set comprises ultrasound signals at successive times in a plurality of spatial points. The set of ultrasound signals is decomposed as a sum of multiple terms. Each term consists of a time-independent spatial component image factor and a space-independent temporal component signal factor. One of ordinary skill in the art will appreciate that hereby a factor may be composite, i.e. may comprise or may be split up into multiple factors. The spatial component images are mutually orthonormal. The temporal component signals are mutually orthogonal. A sharpened spatial image is determined for each spatial component image of multiple spatial component images. A processed image is generated. The processed image is a bilinear combination of determined sharpened spatial images.

In a preferred embodiment, the plurality of spatial points is a multidimensional grid of spatial points. Preferably, the grid is a rectangular grid. Preferably, the set of ultrasound signals comprises ultrasound signals at successive times in each point of a multidimensional rectangular grid of spatial points. Preferably, the multidimensional grid is a two-dimensional or three-dimensional grid of spatial points. Preferably, each spatial point of the multidimensional rectangular grid corresponds to a pixel of the multidimensional rectangular processed image.

In a second aspect, the present invention provides a method for ultrasound imaging, comprising a method according to the first aspect, wherein the step of obtaining the set of ultrasound signals comprises several steps. Ultrasound waves are emitted to said biological tissue of a living subject comprising blood vessels. Ultrasound waves are received at least in part from the biological tissue. Said set of ultrasound signals is obtained based on the received ultrasound waves. Preferably, the emitted ultrasound waves are plane or diverging ultrasound waves. More preferably, the emitted ultrasound waves are a set of plane or diverging ultrasound waves tilted at different angles. Preferably, the received ultrasound waves are backscattered waves off the biological tissue of the set of plane or diverging ultrasound waves. Preferably, the received backscattered waves are coherently compounded.

Some of the method steps may be computer-implemented. The step of decomposing the set of ultrasound signals as a sum of multiple terms is preferably computer-implemented. The step of determining a sharpened spatial image for each of multiple spatial component images is preferably computer-implemented. The step of generating a processed image is preferably computer-implemented. The methods according to the first and second aspects may therefore be computer-implemented methods. In a computer-implemented method according to the first aspect, obtaining the set of ultrasound signals may be receiving the set of ultrasound signals via a communication module. In a computer-implemented method according to the first aspect, obtaining the set of ultrasound signals may be obtaining the set of ultrasound signals via a data acquisition card. In a computer-implemented method according to the first aspect, obtaining the set of ultrasound signals may be reading the set of ultrasound signals from a non-transitory computer-readable storage medium. In a method according to the second aspect, obtaining the set of ultrasound signals comprises emission of ultrasound waves, reception of ultrasound waves, and obtaining the ultrasound signals based on the received ultrasound waves, for example via a data acquisition card. Preferably, the ultrasound signals are computer-readable, more preferably digital, ultrasound signals.

In a third aspect, the present invention provides a computer system for blood vessel image extraction from ultrasound signals. The computer system comprises one or more processors. The computer system is configured for performing a method according the first aspect of the present invention.

In a fourth aspect, the present invention provides a computer program product for blood vessel image extraction from ultrasound signals. The computer program product comprises instructions which, when the computer program product is executed by a computer, such as a computer system according to the second aspect of the present invention, cause the computer to carry out a method according to the first aspect of the present invention. In the fourth aspect, the present invention may furthermore provide a tangible non-transitory computer-readable data carrier comprising the computer program product.

In a fifth aspect, the present invention provides an apparatus for ultrasound imaging of vasculature. The apparatus comprises an ultrasonic wave emitter, an ultrasonic wave receiver, and a computer system according to the third aspect of the present invention. The apparatus is configured for performing the method according to the second aspect of the present invention. Preferably, the apparatus is configured for emitting plane or diverging ultrasound waves via the ultrasonic wave emitter. More preferably, the apparatus is configured for emitting a set of plane or diverging ultrasound waves tilted at different angles via the ultrasonic wave emitter. Preferably, the apparatus is configured receiving ultrasound waves backscattered off biological tissue. Preferably, the apparatus is configured for coherently compounding the received backscattered ultrasound waves.

One of ordinary skill in the art will appreciate that the aspects of the present invention are interrelated. Therefore, every feature disclosed above or below may relate to each aspect of the present invention, even if it has been disclosed in conjunction with a particular aspect of the present invention. One of ordinary skill in the art will furthermore appreciate that several features of the present invention may be disclosed in terms of exemplary mathematical formulae.

The present invention enables resolving small vessels in ultrasound imaging. The present invention in particular solves undesirable blurring when ultrasound waves are scattered off small vessels. The present invention furthermore allows for real-time image acquisition on available computing systems.

FIG. 1 shows a schematic representation of several features of an embodiment of a method according to the present invention. A set of ultrasound signals $s(r_i, t_j)$ of biological tissue of a living subject comprising blood vessels is obtained (101). The set comprises ultrasound signals at successive times (time samples) $t_j$ in a plurality of spatial points $r_i$. The set of ultrasound signals is decomposed as a sum of multiple terms (102):

$$s(r_i, t_j) = \Sigma_{k=1}^{N} \lambda_k p_k(r_i) a_k(t_j).$$

Each term consists of a time-independent spatial component image factor pk and a space-independent temporal component signal factor $\lambda_k a_k$. The spatial component images pk are mutually orthonormal, i.e. pk with $1 \leq k \leq N$ is a set of orthonormal time-independent spatial component images. Mutual orthonormality of the spatial component images over the plurality of spatial points may be expressed as:

$$\Sigma_{i=1}^{N_r} p_k(r_i) p_l^*(r_i) = \delta_{k,l},$$

with Nr the number of spatial points ri in the plurality of spatial points, * denoting complex conjugate, and $\delta_{k,l}$ Kronecker delta: $\delta_{k,l} = 1$ if k equals l, and $\delta_{k,l} = 0$ otherwise. The temporal component signals $\lambda_k a_k$ are mutually orthogonal. Mutual orthogonality of the temporal component signals over the successive times may be expressed as:

$$\Sigma_{j=1}^{N_t} \lambda_k a_k(t_j) \lambda_l a_l^*(t_j) = \delta_{k,l} \lambda_k^2 \Sigma_{j=1}^{N_t} a_k(t_j) a_k^*(t_j),$$

with Nt the number of successive times tj. A sharpened spatial image qk is determined for each spatial component image pk of multiple spatial component images (103). A processed image I is generated (104), being a bilinear combination of multiple sharpened spatial images qk with weight coefficients $\delta_{k,l}$:

$$I(r) = \Sigma_{k,l=n_f=1}^{N} \beta_{k,l} q_k(r_i) q_l^*(r_i).$$

One of ordinary skill in the art will appreciate that in case nf>1, a sharpened spatial image qk may be, but does not have to be, determined for each spatial component image pk with $1 \leq k < nf$.

In a preferred embodiment, each temporal component signal consists of a real-valued positive decomposition coefficient factor and a normalized temporal component signal factor. The normalized temporal component signals are mutually orthonormal. Preferably, the decomposition of the set of ultrasound signals as a sum of multiple terms is performed via a singular value decomposition. A decomposition coefficient is then a singular value. With non-limiting reference to the exemplary mathematical formulae above, ak with $1 \leq k \leq N$ is then a set of orthonormal space-independent temporal component signals, and $\lambda k$ are then the real-valued positive singular values. Preferably, the singular values are arranged in order of decreasing magnitude with increasing decomposition index k: $\lambda_k \geq \lambda_{k+1} > 0$. Mutual orthonormality of the normalized temporal component signals over the successive times may be expressed as:

$$\Sigma_{j=1}^{N_t} a_k(t_j) a_l^*(t_j) = \delta_{k,l}.$$

In a preferred embodiment, a filtering step is performed. The filtering step may comprise application of a high-pass filter to the set of ultrasound signals, preferably prior to the decomposition of the set of ultrasound signals as a sum of terms. This allows for discrimination of slower tissue movement and faster red blood cell movement per spatial point. The filtering step may additionally or alternatively comprise the generation of a processed image without the contribution of one or more of the terms corresponding to the largest decomposition coefficients. With non-limiting reference to the exemplary mathematical formulae above, nf is then larger than one: nf>1. This allows for improved discrimination of slower tissue movement and faster red blood cell movement, as disclosed in the background section above.

In a preferred embodiment, determination of a sharpened spatial image for a spatial component image comprises several steps. Positions of local maxima are determined. A sharpened spatial image is generated, wherein the sharpened spatial image is a linear combination of peak functions. Hereby, each peak function of the linear combination is maximal at the position of one of the local maxima. Preferably, positions of local maxima of the spatial component image are determined.

Preferably, the linear combination of peak functions is a linear combination, over the positions of the local maxima, of a reference peak function shifted to a position of a local maximum and weighted with the value of the spatial component image at the position of the local maximum. Preferably, the reference peak function is proportional to one of a Dirac function or a Gaussian function.

Figure 2:
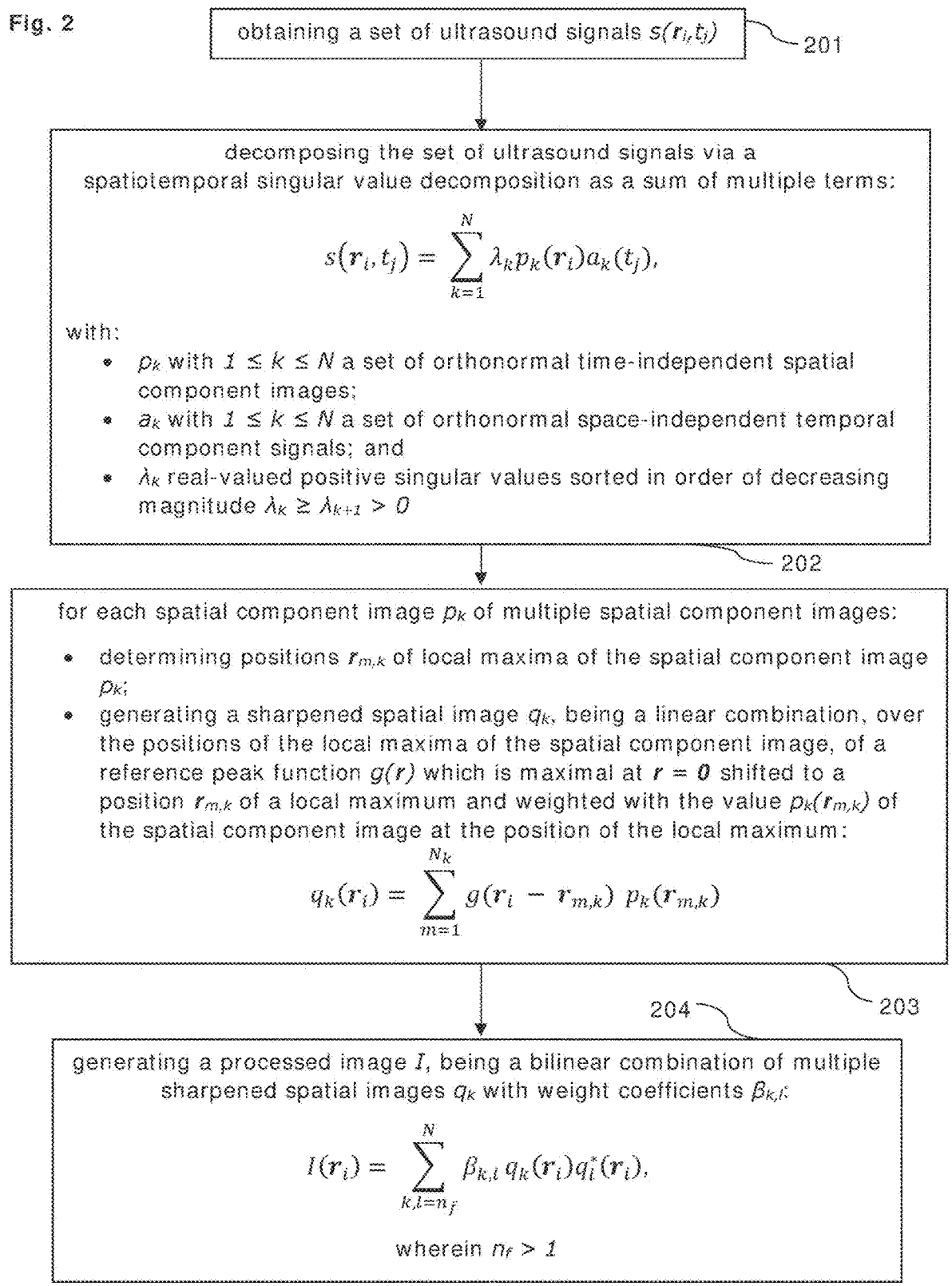
FIG. 2 is a block diagram of a method, according to an example.

FIG. 2 shows a schematic representation of several features of an embodiment of a method according to the present invention. A set of ultrasound signals s(ri,tj) of biological tissue of a living subject comprising blood vessels is obtained (201). The set comprises ultrasound signals at successive times tj in a plurality of spatial points ri. The set of ultrasound signals is decomposed via a spatiotemporal singular value decomposition as a sum of multiple terms (202):

$$s(r_i, t_j) = \Sigma_{k=1}^{N} \lambda_k p_k(r_i) a_k(t_j).$$

Herein, pk with $1 \leq k \leq N$ is a set of orthonormal time-independent spatial component images; ak with $1 \leq k \leq N$ is a set of orthonormal space-independent temporal component signals; and $\lambda k$ are time- and space-independent real-valued positive singular values sorted in order of decreasing magnitude: $\lambda_k \geq \lambda_{k+1} > 0$. For each spatial component image pk of multiple spatial component images (pk with $1 < nf \leq k < N$), a sharpened spatial image qk is generated (203) as follows. Positions rm,k of local maxima of the spatial component image pk are determined. A sharpened spatial image qk is generated. The sharpened spatial image is a linear combination, over the positions of the local maxima of the spatial component image, of a reference peak function g(r) which is maximal at r=0 shifted to a position rm,k of a local maximum and weighted with the value pk(rm,k) of the spatial component image at the position of the local maximum:

$$q_k(r_i) = \Sigma_{m=1}^{N_k} g(r_i - r_{m,k}) p_k(r_{m,k}).$$

Herein, Nk is the number of local maxima of the spatial component image pk. A processed image I is generated (204), being a bilinear combination of multiple sharpened spatial images qk with weight coefficients $\beta_{k,l}$:

$$I(r_i) = \Sigma_{k,l=n_f}^{N} \beta_{k,l} q_k(r_i) q_l^*(r_i).$$

Herein, nf>1. A filtering step is hence performed by generating a processed image without the contribution of one or more of the terms corresponding to the largest singular values of the spatiotemporal singular value decomposition of the set of ultrasound images.

Figure 3:
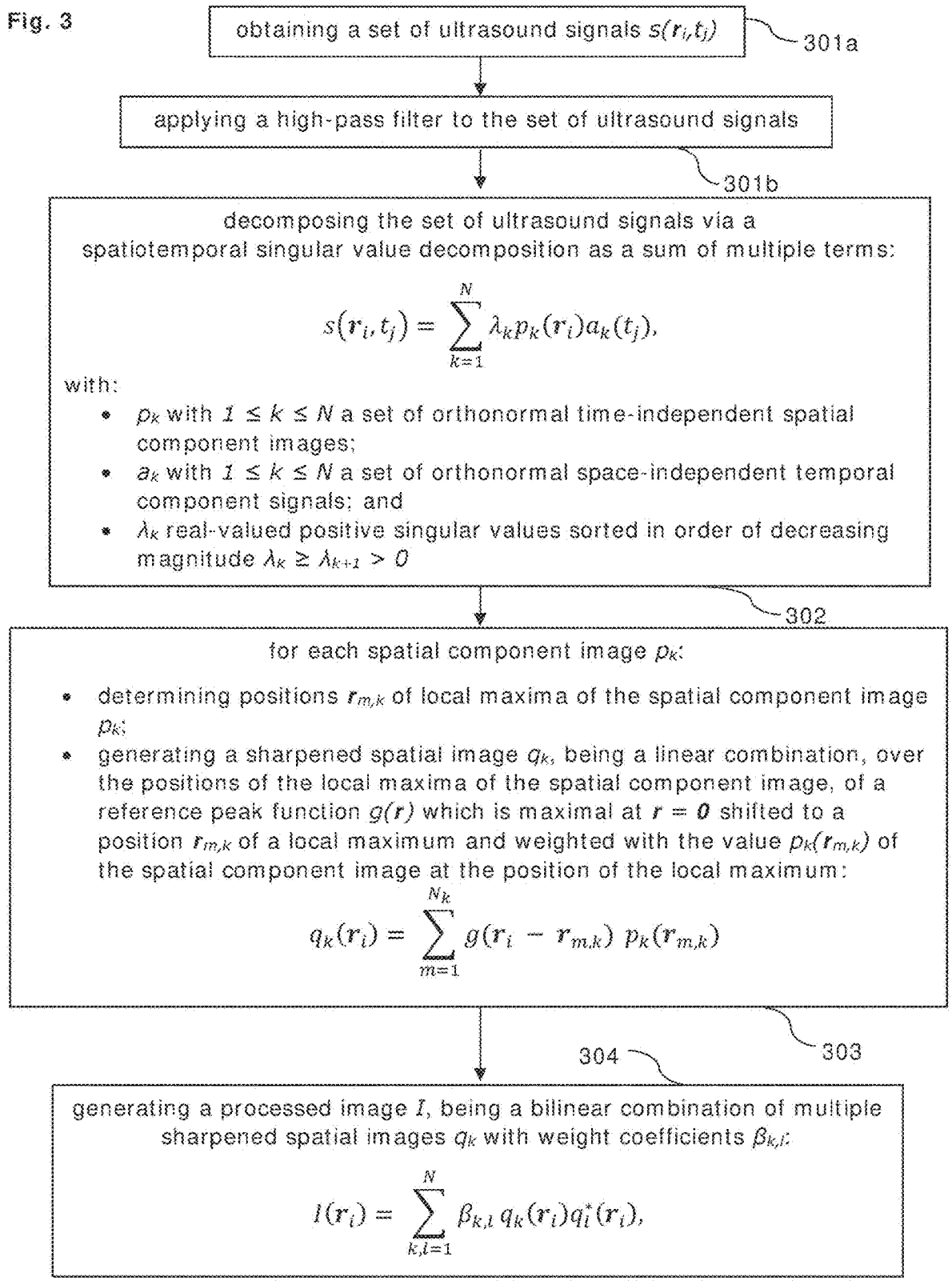
FIG. 3 is a block diagram of a method, according to an example.

FIG. 3 shows a schematic representation of several features of an alternative embodiment of a method according to the present invention. A set of ultrasound signals s(ri,tj) of biological tissue of a living subject comprising blood vessels is obtained (301*a*). The set comprises ultrasound signals at successive times tj in a plurality of spatial points ri. A high-pass filter is applied to the set of ultrasound signals (301*b*), yielding a filtered set of ultrasound signals. The filtered set of ultrasound signals is decomposed via a spatiotemporal singular value decomposition as a sum of multiple terms (302):

$$s(r_i, t_j) = \Sigma_{k=1}^{N} \lambda_k p_k(r_i) a_k(t_j).$$

Herein, pk with $1 \leq k \leq N$ is a set of orthonormal time-independent spatial component images; ak with $1 \leq k \leq N$ is a set of orthonormal space-independent temporal component signals; and $\lambda k$ are time- and space-independent real-valued positive singular values sorted in order of decreasing magnitude: $\lambda k \geq \lambda k+1 > 0$. For each spatial component image pk ($1 \leq k < N$), a sharpened spatial image qk is generated (303) as follows. Positions rm,k of local maxima of the spatial component image pk are determined. A sharpened spatial image qk is generated. The sharpened spatial image is a linear combination, over the positions of the local maxima of the spatial component image, of a reference peak function g(r) which is maximal at r=0 shifted to a position rm,k of a local maximum and weighted with the value pk(rm,k) of the spatial component image at the position of the local maximum:

$$q_k(r_i) = \Sigma_{m=1}^{N_k} g(r_i - r_{m,k}) p_k(r_{m,k}),$$

Herein, Nk is the number of local maxima of the spatial component image pk. A processed image I is generated (304), being a bilinear combination of multiple sharpened spatial images qk with weight coefficients $\beta k,l$:

$$I(r_i) = \Sigma_{k,l=1}^{N} \beta_{k,l} q_k(r_i) q_l^*(r_i).$$

A filtering step is hence performed by applying a high-pass filter prior to the spatiotemporal singular value decomposition.

Most preferably, the peak function is configured to increase the resolution of the vessels. Most preferably, the peak function is configured to obtain an image of the vessels at an image distance scale which is smaller than the ultrasound resolution distance scale. Most preferably, the peak function comprises a decay distance which is smaller than the ultrasound resolution distance.

The following non-limiting list provides several examples of functions to which the reference peak function g(r) may be proportional:
- a Dirac function $\delta(r)$, which equals 1 in r=0 and equals 0 elsewhere;
- a Gaussian function $\exp(-\alpha|r|2)$ with $\alpha$ a real-valued positive scalar, preferably whereby $\alpha$ is larger than the inverse of the square of the ultrasound resolution distance;
- a power function $h(r \neq 0) = \rho|r| - \gamma$ and $h(r=0) = \sigma$ with $\gamma, \rho, \sigma$ a real-valued positive scalars;
- an exponential function $\exp(-\varphi|r|)$ with $\varphi$ a real-valued positive scalar, preferably whereby $\varphi$ is larger than the inverse of the ultrasound resolution distance.

In a preferred embodiment, the weight coefficients of the bilinear combination are calculated based on the mutually orthogonal temporal component signals.

In a first further preferred embodiment, the weight coefficients of the bilinear combination are diagonal in the decomposition index and comprise a magnitude proportional to the square of the 2-norm of the corresponding temporal component signal. In case decomposition coefficients have been obtained, the magnitude of the weight coefficients of the bilinear combination is then proportional to the square of the corresponding decomposition coefficients. This first preferred embodiment corresponds to a blood volume image or power Doppler image obtained based on the sharpened spatial images.

In a second further preferred embodiment, the weight coefficients are proportional to a moment of a product of Fourier transforms of the corresponding temporal component signals. Preferably, the order of the moment equals one. This second preferred embodiment corresponds to an axial blood velocity image or color Doppler image obtained based on the sharpened spatial images.

With non-limiting reference to the exemplary mathematical formulae above, in the first further preferred embodiment the weight coefficients $\beta k,l$ of the bilinear combination are diagonal in the decomposition index k,l and comprise a magnitude proportional to the square of the 2-norm of the corresponding temporal component signal $\lambda k a k$:

$$\beta_{k,l} = \Sigma_{j=1}^{N_t} \lambda_k a_k(t_j) \lambda_l a_l^*(t_j) = \delta_{k,l} \lambda_k^2.$$

With non-limiting reference to the exemplary mathematical formulae above, in the second further preferred embodiment the weight coefficients $\beta k,l$ of the bilinear combination are proportional to a moment of order z of a product of Fourier transforms $\lambda k A k(\omega)$, $\lambda l A l(\omega)$ of the corresponding temporal component signals $\lambda k a k(t)$, $\lambda l a l(t)$:

$$\beta_{k,l} \propto \lambda_k \lambda_l \Sigma_{\omega=\omega_{min}}^{\omega_{max}} A_k(\omega) A_l^*(\omega) \omega^z.$$

Herein, Ak($\omega$) is a Fourier transform of the normalized temporal component signal ak(t), and $\omega$min and $\omega$max are bounds for the interval for the frequency $\omega$. For example: $t_j = (j-1)\Delta t$ (with $1 \leq j \leq N t$); $\omega_x = (x-1)\Delta\omega$ (with $1 \leq x \leq N t$);

$$\Delta\omega = \frac{2\pi}{N_t \Delta t};$$

$$A_k(\omega_x) = \frac{1}{\sqrt{N_t}} \sum_{j=1}^{N_t} a_k(t_j) e^{-i\frac{2\pi}{N_t}(x-1)(j-1)};$$

and $$\beta_{k,l} = \lambda_k \lambda_l (\Delta\omega)^z \sum_{x=1}^{N_t} A_k(\omega_x) A_l^*(\omega_x)(x-1)^z.$$

One of ordinary skill in the art will appreciate that the case z=0 corresponds to the first further preferred embodiment above. Preferably, z=1.

In a preferred embodiment, the apparatus comprises a portable or implantable ultrasound device. The device comprises the emitter and the receiver. The device further either comprises the computer system, or is configured for data communication with the computer system. Preferably, the device is a portable head-mountable ultrasound device, more preferably a portable head-mountable ultrasound helmet. The apparatus may be configured for repetitive generation of a processed image for studying blood flow evolution. The apparatus may be used for functional brain imaging. The apparatus may further comprise one or more physiological sensors, in addition to the ultrasonic receiver, in order to correlate blood flow evolution with physiological data obtained via the physiological sensors. The one or more physiological sensors may comprise one or more physiological sensors from the list comprising a blood oxygen level sensor such as an optical oximeter, a electrophysiological sensor such as an electrocardiograph sensor or electroencephalograph sensor, a respiration sensor, and a temperature sensor such as an infrared temperature sensor. Most preferably, the apparatus comprises an electrophysiological sensor. Preferably, the electrophysiological sensor is configured for electroencephalography.

In a preferred embodiment, the method is performed repetitively for generating multiple processed images for studying blood flow evolution. The method may be used for functional brain imaging. The method may comprise the step of comparing and/or correlating blood flow evolution with electrophysiological recordings. Preferably, the electrophysiological recordings are electroencephalographical recordings.

Any aspect of the present invention may be used for studying blood flow evolution via repetitive generation of a processed image, such as for determining functional responses in a brain. Functional brain imaging may be used to indirectly study brain activation by hemodynamic changes in response to a certain function or stimulus.

Any aspect of the present invention may be used for imaging blood vasculature in a brain, an eye, a heart, a kidney, a liver, a lung, a muscle, a thyroid, or a tumor.

Any aspect of the present invention may be used for computer-implemented anomaly detection, such as via heuristic rules or via classification based on a machine learning algorithm trained with pre-classified data.

Reference is made to E. Mace et al., IEEE Transactions on Ultrasonics, Ferroelectrics, and Frequency Control 60(3), 492-506 (2013), doi: 10.1109/tuffc.2013.2592 for an exemplary disclosure of prior art ultrasound signal acquisition, which may also be used in conjunction with the present invention. The present invention relates in particular to the processing of a set of ultrasound signals, i.e. once a set of ultrasound signals has been obtained. For details of ultrasound signal acquisition used in conjunction with FIGS. 4 and 5 below, reference is made to this prior art document.

Figure 4:
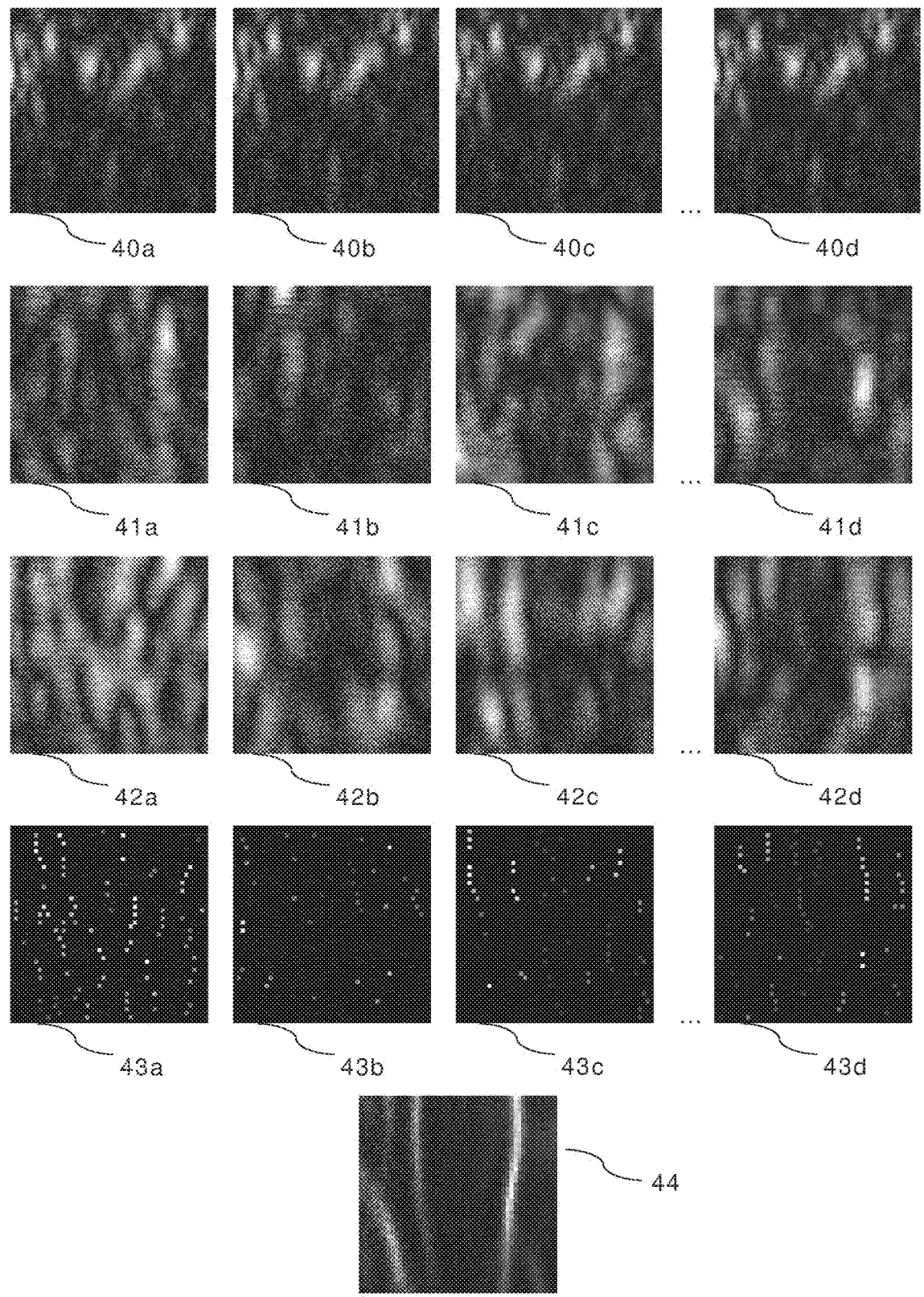
FIG. 4 shows a set of images that illustrate a method, according to an example.

FIG. 4 shows a set of exemplary images to illustrate several steps of an embodiment of a method according to the present invention. An original set of images (40a, 40b, 40c, ..., 40d) is obtained by emission and reception of ultrasound waves. Each image of the set corresponds to a time sample tj. Preferably, at least 100 images, such as 1000 images, have been obtained. Preferably, each image is oversampled at a multiple, preferably at least 4 times, such as 8 times, of the required resolution. The images of the original set appear similar, because most of the signal arises from static tissue. The blood signal is comparatively much weaker (about −40 dB). After a high-pass filter or a spatiotemporal filter, the blood signal is extracted yielding the filtered set of images (41a, 41b, 41c, ..., 41d). The filtered set of images appears to contain a higher degree of dissimilarity due to the random positions of the red blood cells which scatter the ultrasound waves. After the filtering step and the spatiotemporal singular value decomposition (not necessarily in this order as the filtering step may comprise discarding large singular values), a set of orthonormal time-independent spatial component images (42a, 42b, 42c, 42d) is obtained. In each spatial component image, the local maxima are detected, and a sharpened spatial image is obtained comprising just the local maxima (43a, 43b, 43c, 43d). In this case, the reference peak function is a Dirac function. A bilinear combination of the sharpened spatial images is generated (44), with weight coefficients diagonal in the decomposition index and equal to the square of the corresponding singular values.

Figure 5A:
FIG. 5a shows an ultrasound Doppler image obtained with a conventional method, according to an example.
Figure 5B:
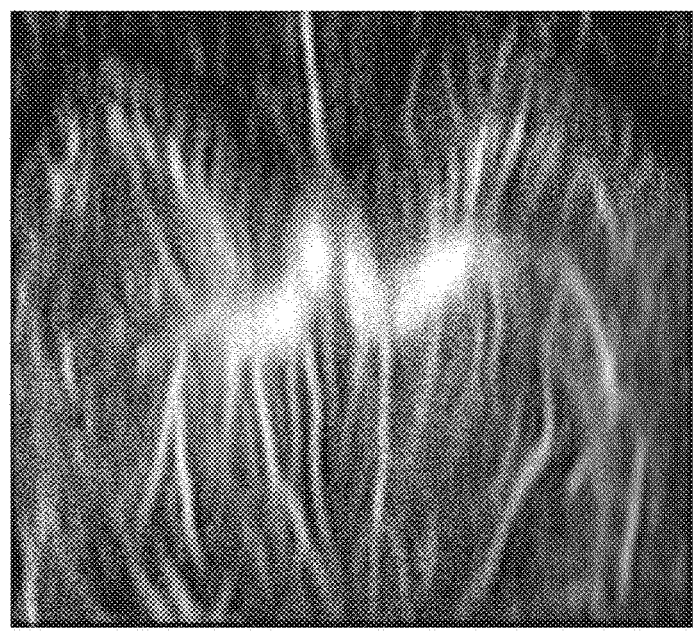
FIG. 5b shows an ultrasound Doppler image obtained with a method according to an example of the present disclosure.

FIGS. 5a and 5b shows two exemplary ultrasound Doppler images. Five times 200 cross-sectional ultrasound images of the rat brain in coronal orientation have been obtained. FIG. 5a shows a typical image of the brain vasculature after computation using a prior art power Doppler method. FIG. 5b presents results on the same dataset of ultrasound signals, obtained with the algorithm disclosed in conjunction with FIGS. 2 and 4. The present invention allows for identification of individual small vessels that cannot be discerned according to the prior art method.

The invention claimed is:

1. A method comprising:
obtaining a set of ultrasound signals at successive times at a plurality of spatial points within biological tissue;
decomposing the set of ultrasound signals into multiple terms of a sum, wherein the multiple terms include respective spatial component image factors and respective temporal component signal factors, wherein spatial component images corresponding to the spatial component image factors are mutually orthonormal, and wherein temporal component signals corresponding to the temporal component signal factors are mutually orthogonal;
determining sharpened spatial images for each of the spatial component images; and
generating a processed image including a bilinear combination of the sharpened spatial images.

2. The method of claim 1, wherein determining the sharpened spatial images comprises:
determining positions of local maxima within the spatial component images; and
generating the sharpened spatial images as a linear combination of functions that each have a corresponding maximum at the positions of the local maxima within the spatial component images.

3. The method of claim 2, wherein the linear combination is a linear combination over the positions of the local maxima of a reference peak function which is weighted with a value of the spatial component images at the positions of the local maxima.

4. The method of claim 3, wherein the reference peak function is proportional to a Dirac function.

5. The method of claim 3, wherein the reference peak function is proportional to a Gaussian function.

6. The method of claim 1, wherein the temporal component signals include respective real-valued positive decomposition coefficient factors and respective normalized temporal component signal factors, wherein the normalized temporal component signal factors are mutually orthonormal, wherein the real-valued positive decomposition coefficients are arranged in decreasing magnitude with increasing decomposition index, and wherein one or more of the terms corresponding to the largest decomposition coefficients do not contribute to the processed image.

7. The method of claim 1, wherein the plurality of spatial points is a multidimensional grid of spatial points.

8. A computer system configured for blood vessel image extraction from ultrasound signals, the computing system comprising one or more processors, the computing system configured for performing the method of claim 1.

9. An apparatus for ultrasound imaging of vasculature, comprising an ultrasonic wave emitter, an ultrasonic wave receiver, and a computer system, wherein the apparatus is configured for performing the method according to claim 1.

10. The apparatus according to claim 9, comprising a portable or implantable ultrasound device that includes the ultrasonic wave emitter and the ultrasonic wave receiver.

11. A non-transitory computer readable medium for blood vessel image extraction from ultrasound signals, the non-transitory computer readable medium comprising instructions which, when executed by a computer, cause the computer to carry out the method according to claim 1.

12. The method of claim 1, wherein the set of ultrasound signals originate from blood vessels of a subject.

13. The method of claim 1, wherein the spatial component image factors are time-independent.

14. The method of claim 1, wherein temporal component signal factors are space-independent.

15. The method of claim 1, wherein terms of the bilinear combination are weighted relative to each other with weight coefficients.

16. The method of claim 15, wherein the weight coefficients are diagonal in a decomposition index.

17. The method of claim 15, wherein the weight coefficients have a magnitude proportional to a square of a 2-norm of the corresponding temporal component signal.

18. The method of claim 15, wherein weight coefficients are proportional to a moment of a product of Fourier transforms of the corresponding temporal component signals.

19. The method of claim 18, wherein an order of the moment is one.

20. The method of claim 1, wherein obtaining the set of ultrasound signals comprises emitting plane waves toward the biological tissue.

\* \* \* \* \*